United States Patent
Neuberger et al.

(10) Patent No.: US 8,999,933 B2
(45) Date of Patent: Apr. 7, 2015

(54) PHOTODYNAMIC COSMETIC PROCEDURE AND HEALING METHOD

(75) Inventors: Wolfgang Neuberger, F.T. Labuan (MY); Volker Albrecht, Jena (DE); Danilo Castro, Montevideo (UY)

(73) Assignee: Biolitec Pharma Marketing Ltd, F.T. Labuan (MY)

( * ) Notice: Subject to any disclaimer, the term of this patent is extended or adjusted under 35 U.S.C. 154(b) by 0 days.

(21) Appl. No.: 11/650,207

(22) Filed: Jan. 5, 2007

(65) Prior Publication Data

US 2007/0166369 A1    Jul. 19, 2007

Related U.S. Application Data

(60) Provisional application No. 60/759,660, filed on Jan. 18, 2006.

(51) Int. Cl.
| | |
|---|---|
| A61K 9/127 | (2006.01) |
| A61K 8/65 | (2006.01) |
| A61K 8/49 | (2006.01) |
| A61K 31/407 | (2006.01) |
| A61K 31/555 | (2006.01) |
| A61L 27/24 | (2006.01) |
| A61L 27/54 | (2006.01) |
| A61Q 19/06 | (2006.01) |
| A61Q 19/08 | (2006.01) |
| A61K 41/00 | (2006.01) |
| A61K 38/00 | (2006.01) |

(52) U.S. Cl.
CPC ............... *A61K 8/65* (2013.01); *A61K 9/1271* (2013.01); *A61K 8/4946* (2013.01); *A61K 31/407* (2013.01); *A61K 31/555* (2013.01); *A61L 27/24* (2013.01); *A61L 27/54* (2013.01); *A61Q 19/06* (2013.01); *A61Q 19/08* (2013.01); *A61K 41/0071* (2013.01); *A61K 2800/434* (2013.01); *A61K 2800/81* (2013.01); *A61L 2300/414* (2013.01); *A61L 2300/604* (2013.01)

(58) Field of Classification Search
CPC .................................................... A61K 9/1271
See application file for complete search history.

(56) References Cited

U.S. PATENT DOCUMENTS

| | | | | |
|---|---|---|---|---|
| 4,433,043 | A * | 2/1984 | Sawada et al. | 430/175 |
| 4,947,840 | A | 8/1990 | Yannas et al. | |
| 5,552,452 | A * | 9/1996 | Khadem et al. | 522/63 |
| 5,913,884 | A | 6/1999 | Trauner et al. | |
| 6,107,466 | A | 8/2000 | Hasan et al. | |
| 6,165,205 | A | 12/2000 | Neuberger | |
| 6,527,764 | B1 | 3/2003 | Neuberger et al. | |
| 6,607,522 | B1 * | 8/2003 | Hamblin et al. | 606/8 |
| 6,730,692 | B2 * | 5/2004 | Hellstrand et al. | 514/400 |
| 7,282,215 | B2 * | 10/2007 | Chowdhary et al. | 424/450 |
| 7,375,215 | B2 * | 5/2008 | Bradley et al. | 540/145 |
| 2001/0010826 | A1 * | 8/2001 | Usala | 424/484 |
| 2003/0224002 | A1 * | 12/2003 | Hasan et al. | 424/178.1 |
| 2005/0038471 | A1 * | 2/2005 | Chan et al. | 606/214 |
| 2005/0048109 | A1 * | 3/2005 | Albrecht et al. | 424/450 |
| 2006/0088584 | A1 * | 4/2006 | Albrecht et al. | 424/450 |
| 2008/0194520 | A1 * | 8/2008 | Swinnen et al. | 514/63 |
| 2009/0012211 | A1 * | 1/2009 | Abecassis | 523/128 |

OTHER PUBLICATIONS

Arizona Chemical BASF et al. (2001) The flavor and fragrance high production volume consortia, The Terpene Consortium, test plan for terpenoid tertiary alcohols and related esters, pp. 1-3.*
Hashizaki et al. (2003) Effects of poly(ethylene glycol) (PEG) chain length of PEG-lipid on the permeability of liposomal bilayer membranes, Chem. Pharm. Bull. (Tokyo), vol. 51, No. 7, pp. 815-820.*
Behrens et al. (1985) Physiological adaption in the synthesis of the extracellular polysaccharide xanthan, Acta Biotechnol., vol. 5, No. 1, pp. 109-113.*
Harris et al. (2003) Effect of pegylation on pharmaceuticals, Nature Rev. Drug Discovery, vol. 2, pp. 214-221.*
Giebink et al. (1978) Serum opsonic deficiency produced by *Streptococcus pneumoniae* and by capsular polysaccharide antigens, Yale J. Biol. Med., vol. 51, No. 5, pp. 527-538.*

(Continued)

*Primary Examiner* — Manjunath Rao
*Assistant Examiner* — Samuel Liu
(74) *Attorney, Agent, or Firm* — Bolesh J. Skutnik; B J Associates

(57) ABSTRACT

Innovative non-surgical methods and compositions are provided for administering PDT to promote tissue regeneration or augmentation while minimizing scarring and risk of infection. Among several areas of application, is the treatment of acute and chronic wounds which have afflicted epidermal and connective tissue layers of the body. Another application area is as cosmetic surgery/treatments, including: reducing wrinkles, sulcus, scars (acne or traumatic caused), sequelae cellulite, as well as for other skin irregularities, to give a smoother skin surface. This invention consists of a collagen based or other suitable biodegradable supporting matrix which is embedded with a liposomal loaded photosensitizer. In one embodiment of this invention a liposomal formulated photosensitizer is first injected at the site followed by collagen implantation and PDT treatment. In another embodiment a liposomal formulated photosensitizer is incorporated in the collagen. Generally 30 minutes after collagen is mixed with photosensitizer the light activation is done. The matrix may also carry important growth factors and cytokines, which promote fibroblast cell migration and proliferation, to the wound site. Microbial infection at the wound site can also be controlled by antibacterial PDT.

9 Claims, 2 Drawing Sheets

(56) References Cited

OTHER PUBLICATIONS

Nair et al. (2005) "Polymers as Biomaterials for Tissue Engineering and Controlled Drug Delivery", Adv. Biochem. Engineer. Biotech., vol. 102, pp. 47-90.*

Intergra Dermal Regeneration Template, Information for Patients and Families, Ethicon, (date unk.), 11 pages.

Zyplast Collagen Implant Physican Package Insert, McGhan Medical Corporation, 48490 Melmont Drive, Fremont, CA 94538, 2 pages, (unk date).

* cited by examiner

PHOTODYNAMIC COSMETIC PROCEDURE AND HEALING METHOD

DOMESTIC PRIORITY UNDER 35 USC 119(e)

This application claims the benefit of U.S. Provisional Application Ser. No. 60/759,660 filed Jan. 18, 2006, entitled "PhotoDynamic Cosmetic Procedure and Healing Method" by Volker Albrecht, Danilo Castro and Wolfgang Neuberger, which is incorporated by reference herein.

BACKGROUND OF THE INVENTION

1. Field of the Invention

The present invention generally relates to photodynamic therapy for wound healing and cosmetic application, particularly to methods and compositions that will enhance the healing process of injured epidermal and connective tissue wounds, thus promoting tissue reconstruction and augmentation.

2. Information Disclosure Statement

A wound is a disruption of skin tissue integrity causing loss of function in the region. A wound can be simple like minor cuts or abrasion involving the epidermal and superficial dermal layers and is termed as partial-thickness wound. This heals faster by re-epithelialiazation; while complicated/full thickness wounds are deeper injuries to the skeletal system, the muscle tissue or even to the inner organs. Wounds can be a traumatic wound like abrasion, contusion, laceration; or a surgical wound-skin graft, post-surgical incisions which are easiest to heal; or its can be chronic/non-healing wound like pressure sores, or diabetic ulcers which are more difficult to heal. Injuries to connective tissue like bone, cartilage are also very common. Finally burn injuries especially of the second and third degree, where tissue loss results in scarring and disfigurement and delays the healing process, are also a major concern.

Wound healing is a dynamic process involving physiological, biochemical and morphological alterations. The process of repair and reconstruction following injury is one of the most fundamental defense mechanisms against environment. This healing process consists of an orderly progression of events that reestablish the integrity of the damaged tissue. It comprises separate yet overlapping phases namely—hemostasis, inflammation, proliferation, angiogenesis and remodeling by accumulation of matrix and necessary cells to heal the injured part. All healthy living organisms have an innate ability to heal the wounds. But in certain cases wounds may not heal easily or there is a delay due to impaired immunity, poor health conditions, and/or poor nutrition; for example in diabetic patients wound healing is impaired and even a simple cut can manifest into a chronic wound if immediate medical care is not provided. New technologies are being developed to improve the healing in these conditions.

Wound healing is a complex process involving a variety of different cells, proteins, chemo-attractants, proteinases, inflammatory cells, cytokines and growth factors. Healing process is regulated by growth factors and cytokines that affect cell migration, proliferation and protein production. Immediately after injury, the wound fills with blood and a clot is formed to stop bleeding. If tissues are damaged, a cascade of cellular events is initiated to prepare the injured area for the deposition of collagen, which ultimately will replace damaged tissues. During inflammatory phase the bleeding is controlled and immune system is activated to control the bacterial infection; and granulation tissues are formed during the proliferative phase which covers the injured area. This is followed by angiogenesis and remodeling.

Understanding the function of cytokines, growth factors, and other mediators involved in wound healing process can help us manipulate these component to heal the wound faster thus improving function and aesthetics. Conventional methods of local wound treatment which is most widely practiced consists of mechanical cleaning, disinfection with antiseptic solutions, wound debridement, wound closure, antibiotic treatments, and wound closure by surgical methods.

Wound healing is controlled via a combination of three mechanisms: contraction, epithelialization, and connective tissue deposition. Wound-type (i.e. abrasions, lacerations, etc.) will determine which of these three mechanisms will emerge as the predominate mechanism in the healing process. For example, the healing of abrasions is predominated by epithelialization, whereas for sutured lacerations the principle mechanism is connective tissue deposition. Closing wounds by surgical methods remains the best way of promoting wound healing, however, not all wounds are suited for surgical intervention. Anatomical location as well as the surface area and/or depth of a wound can make surgical methods of wound closure impossible or impractical. Moreover, the tissue removal and scarring that follows some surgical methods can be highly disfiguring and debilitating. Extensive wounds, such as burns, restrict limb movement or function as a result of skin contractures due to the shrinking of scar tissue in the skin or connective tissues at the wound site.

Latest treatment method is use of tissue engineered 'skin substitutes'. Wherein scientist have developed grafts using sheet of fibroblasts embedded in biodegradable matrix, sheet of cultured kerationcytes and dual layered dermal/epidermal engineered skin. One such example is use of Integra artificial skin (developed by Burke and Yannas in 1980s). Yannas at al in his U.S. Pat. No. 4,947,840 disclose the use of this biodegradable artificial skin implant for delaying the contraction and promoting tissue regeneration in burn wounds with tissue loss. Integra DRT can only replace deeper skin layer of deimis and still require a skin graft to cover it and prevent from infection.

Many such products have been approved by FDA (examples: Integra DRT, TransCyte). Integra Dermal Regeneration Template (DRT) is a cell free matrices comprising of porous collagen/chondritein-6 sulphate matrix overlaid with thin silastic sheet. This template acts as a framework for dermal regeneration thus inhibiting scaring and promotes healing. Like cell-free matrix, cell-containing matrices are also used for grating; examples are Dermagraft, Apligraf, and Hyalograft-3D (skin grafts comprised of semi-artificial dermis) etc. Even destruction of bone and cartilage tissue due to disease and inefficient bone healing after traumatic injury may be addressed by tissue engineering techniques. But tissue engineered skin grafts are expensive and timely for lager scale production. Some times this skin graft show poor take rate and often fails to graft onto the patients.

Recently, there has been considerable interest in the effects of light on wound healing. Certain lasers have proven to be an efficacious, noninvasive method of accelerating the healing process. For example, the use of high powered 980 nm lasers to accelerate wound healing was described by Neuberger in U.S. Pat. No. 6,165,205. Thus, laser assisted wound healing would make an attractive alternative to surgical methods. Photodynamic therapy ("PDT") is another laser treatment method that uses specific wavelength irradiation to activate a photosensitizer drug. Photoactivation of the drug induces localized oxidative damage in the diseased tissues where the photosensitizer has preferentially accumulated. PDT is thought to have a positive effect on the wound healing process as well.

As the consequence of continual research in the field of wound healing it is found that light therapy can improve tissue healing. Low power laser energy has been used for wound healing as it can apparently elicit a cellular response thus promoting healing process. U.S. Pat. No. 6,165,205 by Neuberger discusses the use of high power non-ablative laser to accelerate wound healing. A 980 nm diode laser is employed here to activate fibroblast cells and collagen synthesis at the wound site to promote wound healing. While in U.S. Pat. No. 6,527,764 by the same inventor a device is described for laser treatment that combines activating laser power with bio-modulation power to enhance tissue healing and regeneration after treatment.

In the last decade, low energy light source have been used to treat wounds or lesions in a variety of tissues. Low level lasers especially He—Ne lasers have been found to promote epithelization in full thickness wounds. In fact NASA has developed a handheld LED which greatly enhances wound healing and musculoskeletal injuries. LED and Low Level Laser therapy have been found to increase fibroblast proliferation in vitro (Vinck et al). Studies using low power light sources from visible, near infrared or near ultraviolet (UVA) light have been shown to be effective in promoting cell proliferation and growth while a high energy light can inhibit cell growth.

For example, a PDT method for modulating the healing process in unhealed or partially healed wounds has been described by Trauner et al. in U.S. Pat. No. 5,913,884. Trauner et al. disclose and claim a high dose PDT method for inhibiting fibrosis, the rapid production of dense bands of collagen during the healing process. Trauner describes a three step process involving light irradiation of the wound site after the administration of a photosensitizer conjugated to a targeting moiety that is specific for macrophages or myofibroblasts.

Hasan et al. disclose a low dose PDT method for accelerating wound healing in U.S. Pat. No. 6,107,466. Hasan's PDT method requires a three step process involving light irradiation of the wound site after the administration of a photosensitizer and is purported to stimulate the secretion of growth factors in cells at a wound site. Moreover, Hasan et al. claim a PDT method that accelerates wound healing without causing tissue destruction.

PDT is a new treatment modality used for treating certain type of cancers, however the use of PDT in healing and scar removal is under intense research but not fully explored. Resistant bacterial growth in the wound site needs to be controlled to promote healing. Ultraviolet light (UVA) have been reported to kills this bacterial cells. While in PDT treatment methods, the PS may be tagged to target specifically bacterial cells so that photoactivation reaction will destroy the bacterial cells.

Use of PDT in wound healing process has been reported in U.S. Pat. Nos. 6,107,466 and 5,913,884 by Hasan et al and Trauner et al respectively. U.S. Pat. No. 6,107,466 describes a PDT treatment method for accelerating healing process in unhealed and partially healed wounds. In this patent an effective dose of PDT is selected to stimulate production of growth factors without damaging the cells to promote healing at the wound site. Trauner et al. in their patent (U.S. Pat. No. 5,913,884) describe a three step PDT method to treat unhealed and partially healed wounds by either inhibiting fibrosis by using high dose PDT or hastening the healing process by low dose PDT.

While these references discuss PDT in connection with wound healing, none of them describe or disclose how or why a PDT method, for cases where tissue augmentation or replacement is a key factor with attendant wound healing, would be beneficial or could be used. Beyond that there are many examples where for 'wound-free', healthy tissue there are times where enhancement of the 'healthy tissue' by tissue augmentation or replacement is particularly desired.

Accordingly, there is an urgent need for a reliable and practical method of tissue repair and wound closure that is appropriate for full or partial thickness wounds such as burns or chronic ulcerations. For wounds where tissue augmentation or replacement is necessary a non-surgical treatment method that promotes or accelerates the healing process while minimizing scarring and the risk of infection is highly desirable. The present invention addresses this need.

The present invention, aims at overcoming the above discussed drawbacks of currently used treatment procedures for healing complicated wounds. This invention provides minimally invasive non-surgical PDT based treatment method that promotes wound healing and minimizes scarring. Furthermore this invention is not only for all types of partial and full thickness wounds, but also to reduce scars, wrinkles and other skin imperfection or cosmetic conditions.

OBJECTIVES AND BRIEF SUMMARY OF THE INVENTION

It is an objective of the present invention to provide a composition and PDT method for wound healing by tissue replacement or augmentation reducing the healing time and minimizing scar formation.

It is another objective of the present invention to provide a tissue matrix, which is collagen or otherwise biodegradable-based supporting tissue, to initiate cell proliferation and/or wound reconstruction.

It is also another objective of this invention to use Laser/Non-laser light source for healing wounds during post PDT treatment period It is the aim of this invention to facilitate faster healing of cancer wounds treated by PDT using collagen matrix.

It is also the aim of this invention to use collagen matrix and PDT for cosmetic purpose such as reducing wrinkles, fine lines, scars (acne or traumatic) and other skin imperfections.

It is also an objective of this invention to provide liposomal loaded PS entrapped in the tissue matrix which is conjugated to biomolecules to target specific cells.

It is yet another object of the present invention to provide a non-surgical method of wound healing.

It is still another objective to provide composition and methods to prevent bacterial growth at the wound site during healing and recovery.

It is further objective to impregnate the tissue matrix with growth factors cytokines and other cellular component which are required for tissue healing.

Briefly stated, the present invention provides innovative non-surgical methods and compositions for administering PDT to promote tissue regeneration or augmentation while minimizing scarring and risk of infection. Among several areas of application, is the treatment of acute and chronic wounds which have afflicted epidermal and connective tissue layers of the body. Another application area is as cosmetic surgery/treatments, including: reducing wrinkles, sulcus, scars (acne or traumatic caused), sequelae cellulite, as well as for other skin irregularities, to give a smoother skin surface. This invention consists of a collagen based or other suitable biodegradable supporting matrix which is embedded with a liposomal loaded photosensitizer. In one embodiment of this invention a liposomal formulated photosensitizer is first injected at the site followed by collagen implantation and PDT treatment. In another embodiment a liposomal formulated photosensitizer is incorporated in the collagen. Generally 30 minutes after collagen is mixed with photosensitizer the light activation is done. The matrix may also carry important growth factors and cytokines, which promote fibroblast cell migration and proliferation, to the wound site. Microbial infection at the wound site can also be controlled by antibacterial PDT.

The above and other objects, features and advantages of the present invention will become apparent from the following description read in conjunction with the accompanying drawings.

DETAILED DESCRIPTION OF PREFERRED EMBODIMENTS

Figure 1:
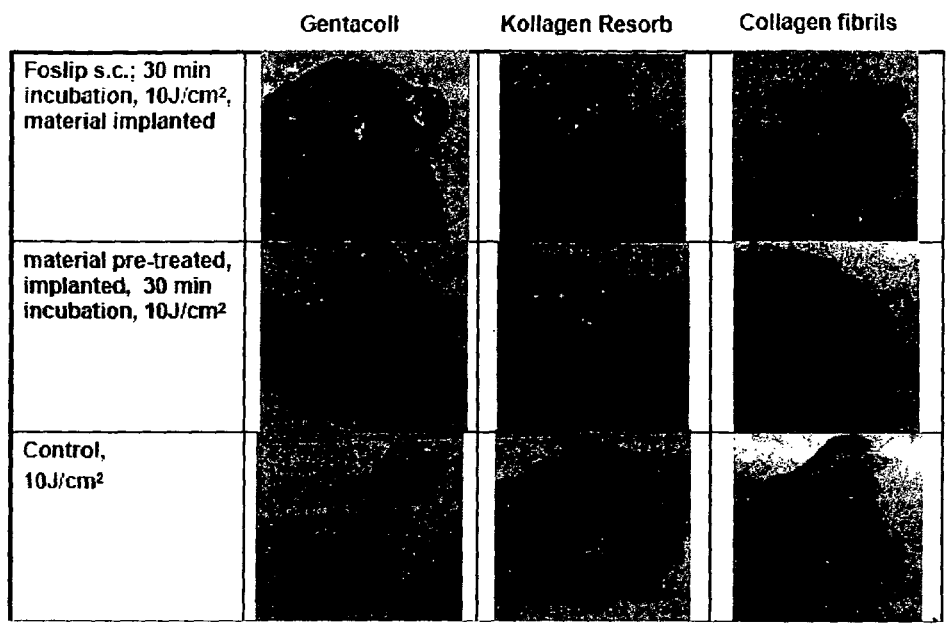
FIG. 1 shows biopsy results 14 days after treatment in mice.

A wound is the disruption of the anatomic structure and its function in any part of the body. While healing is the restoration of that structure and function and it is a continuum of complex interrelated processes involving different type of cells, growth factors extra-cellular matrix etc. Wound healing process is impaired in certain cases resulting in unhealed wounds. The reason for delayed or unhealed wound can be impaired wound healing process, health and nutritional condition of the patient, age, oxygen supply to the wound site etc.

In the last few decades, many different kinds of therapies have been developed to promote faster healing of wounds. Latest being tissue engineered 'skin graft', low level light therapy and Photodynamic therapy (PDT). Photodynamic therapy (PDT) using light source has been shown to enhance wound repair.

The present invention provides a suitable PDT method and Collagen or biological based supporting matrix embedded with suitably formulated photosensitizers in liposomes, Pegylation Pegylated liposomes. etc. to improve healing process. This method can be applied to effectively treat burn injuries, to repair damaged cartilage surface within the knee and the repair to the surface of the vascular damages, Vascular venous and arterial ulcers, fail sutures or secondary cicatrisation and to reduce skin imperfection like scars, winkles and other cosmetic condition.

The term collagen used includes Auto, Alio, synthetic and semi-synthetic collagen examples which includes Chondro-Gide®, Chondrocell®, Gentacoll, Kollagen Resorb (Resorba GmbH) and Collagen Fibrils (Collagen Matrix Inc). Kollagen Resorb. The collagen used is based on the type of injury being treated.

The word photosensitizer, as used herein, includes photosensitizing agents, Photosensitizing delivery systems, and photosensitizer derivatives from a parent structure or a prodrug selected from the group consisting of: porphyrin, porphyrinogen, hematoporphyrin, pheophorbide, chlorin, bacteriochlorin, iso-bacteriochlorin and dihydro- and tetrahydro-tetrapyrroles.

In one of the embodiment of this invention a collagen based or other biodegradable supporting tissue matrix is placed at the wound site or injected under the skin. This supporting matrix has dermal component similar to the natural human skin. The photosensitizer (PS) is loaded into a liposome to ensure controlled drug delivery at the site, this PS loaded liposomes are impregnated in the tissue matrix. In addition to this, the tissue matrix also consists of important growth factors like epidermal growth factor, platelet derived growth factor, tissues angiogenesis growth factor and cytokines, keratinocytes and also fibroblasts to fasten the healing process. The GFs and cytokines control key cellular activities including cell division, differentiation and tissue repair.

In this invention different types of collagen sponges like Gentacoll, Kollagen Resorb (Resorba GmbH) and Collagen Fibrils (Collagen Matrix Inc)] where used with PDT for healing different types of wound and to improve cosmetic appearance of the skin surface. In case of wrinkle reduction on face and neck region injectable formulation of collagen is required for best cosmetic effect. Collagen is injected through tiny needle just below the surface of the skin to smooth wrinkles. Examples of injectable collagen are Zyplast and Zyderm (produced by Inamed Aesthetics Inc. USA). Zyplast and zyderm is derived from collagen of cow skin.

Furthermore, a variety of Hyaluronic acid, a non-animal stabilized hyaluronic acid, can also be used as collagen is used above to correct wrinkle, scars and other skin deformities for aesthetic purpose. Hyaluronic acid is a substance found naturally in the human body. It is hydrophilic in nature, hence acts as a sponge to absorb water and provide long lasting results when used as filler with low risk of allergic reaction.

Figure 2:
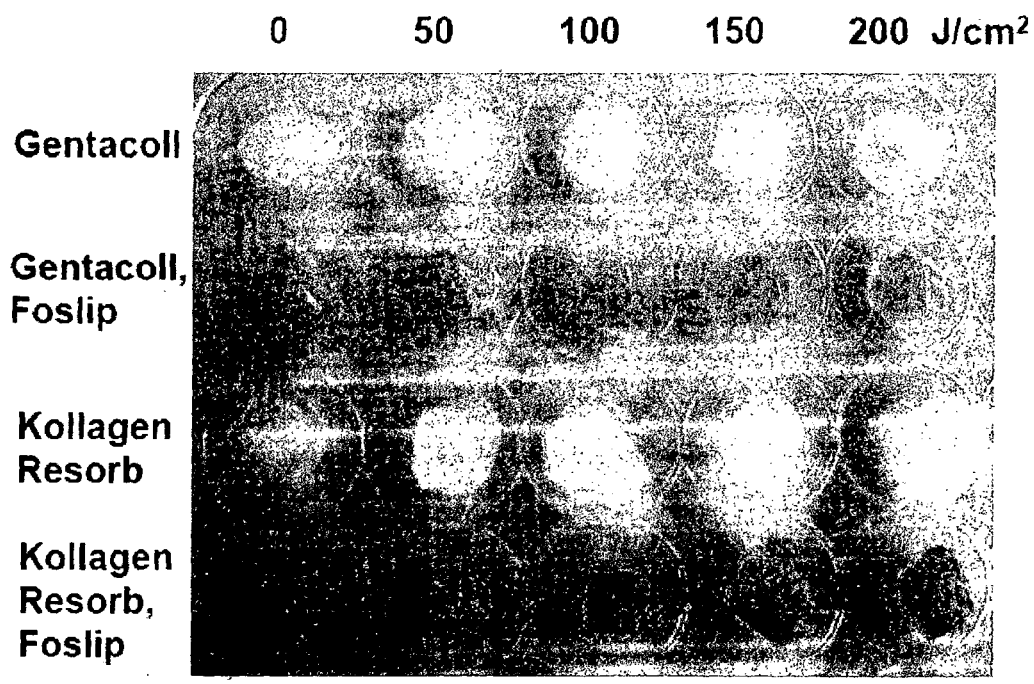
FIG. 2 macroscopic picture of thermic stability of collagen during laser irradiation.
Figure 3:
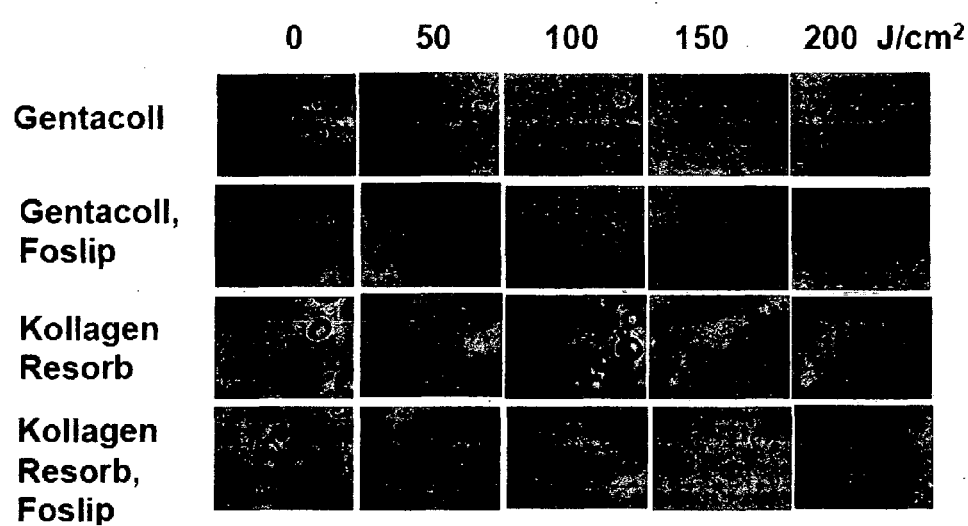
FIG. 3 the thermic stability of collagen when exposed to different energy levels at microscopic level.

FIGS. 2 and 3 give the macro and microscopic pictures of thermic stability in the collagen and collagen with liposome loaded mTHPC when exposed to different energy levels.

The collagen stability was tested for a range of energy levels (0 to 200 $J/cm^2$), FIGS. 2 and 3 illustrates in-vitro experimental results of collagen stability at different energy levels. It was noticed in the experiments that collagen structure is not changed at high light dose. Thus it was shown that this collagen material can be used even at higher light doses without affecting/damaging the collagen structure.

Zyplast and zyderm has been used to remove wrinkle, scares, deep furrows and other skin irregularities but there effect last only for a period of 3-6 months. In the present invention Collagen matrix is used in combination with PDT to improve cosmetic effect and also their durability. The PDT stimulates natural collagen producing cell in the region, and achieve the fact that the engrafted collagen incorporate the skin's collagen, it itself explains its bigger durability In one of the embodiment, this invention is used for skin resurfacing and for cosmetic reasons which includes correction of contour deformities, winkles reduction, acne scare, pits, surgically induced irregularities and other soft-tissue defects. As a result of aging dermis loses collagen and elastin over the time, as the result of which skin gets thinner and uneven resulting in wrinkles. Wrinkles can be just fine lines or deep furrows on the skin. Other factors promoting wrinkles are smoking, sun damage (photo aging), dryness and loss of moisture, skin color (light colored skin are more prone to develop wrinkles), and heredity etc.

In further embodiment of this invention Laser/non-laser light source is used with PDT and collagen matrix. After administering PDT and collagen to the wound site, Laser light of 980 nm is used for biostimulating the treated area for hastening the healing and reducing the scar formation. Laser light 980 is used too for to fill first to edema and after to increase the collagen matrix when is apply directly in the sub cutaneous cellular tissue using a 200μ fiber optic with low power and high shoot duration, beside the 980 nm external use with a fiber with micro lent point reduce too the fines per oculars wrinkles in their first stages.

Animal Studies

18 Balb c mice were used for the study. Selected mice were narcotized and a small cut was inflicted in the neck region. Three treatment groups were are set up: in the first treatment group a 5×5 mm piece of collagen saturated with liposomal formulation of mTHPC is implanted under the skin. After 30 min of incubation the area is irradiated with light at 652 nm at 10 J/cm$^2$ after which the region is covered with catgut and Hansaplast plaster spray.

In second group 50 μl liposomal formulation of mTHPC is injected subcutaneously and is incubated for 30 min followed by irradiating with light at 652 nm at 10 J/cm$^2$ followed by implanting non-treated collagen material under the skin opened by small cut. After which the region is covered and protected.

Third group is the control where in the mice wound is treated using collagen and laser irradiation with no liposomal formulation of mTHPC.

Collagen products used in this treatment includes Genta-coll, Kollagen Resorbs and collagen fibrils. In all the treatment groups 2 mice each is treated, for, each of these collagen products.

The treated mice were kept under observation to record the progress in wound healing. The progress in the wound healing process was recorded after 24 hours, 48 hours, 5 and 12 days. It was noticed that all mice in treatment group 2 showed very good response with slight inflammation and wound was healed well; with all animals being vital in the group. while mice in treatment group 1 had shown strong redness and inflammation with hair loss in the treated area but the wound healing process was good by 12 days with hair growing back in the areas if treatment. Control group 3 showed very strong inflammatory action with redness and strong swelling in the initial period of treatment. All mice treated with collagen fibrils showed best biocompatibility compared to other collagen products used.

FIG. 1 show the biopsy results of the treated mice after 14 days for the three groups with three different collagen products used. When the wound was pretreated with liposomal formulation of mTHPC enhanced vascularisation was observed.

"Further variation of this invention is to treat atherosclerotic vascular disease. Atherosclerotic vascular disease represents one of the major health problems in the world; atherosclerosis is abnormal thickening and hardening of the arteries caused by deposit of fatty acid on inner lining of blood vessels forming atheromatous plaque. In the present invention photosensitizers are targeted at atheromatous plaque followed by irradiation with light energy of suitable wavelength to initiate cytotoxcity effect on abnormal proliferating smooth muscle cells and control microbial growth in lesion."

The present invention is further illustrated by the following examples, but is not limited thereby.

Example 1

For Wound Healing

The wounded region is cleaned and irrigated with sterile or saline water to remove the cell debris, necrotic and damaged cells, and cell exudates and to decrease the bacterial infection. Debridement of chronic wounds needs to be done often as the non-viable cells and dead cells need to be removed to prevent bacterial infection and promote granulation tissue formation, thus accelerating the healing process. After initial cleaning of the wound bed with aseptic solution the collagen based supporting matrix is applied to the wound bed. After certain time interval the site is irradiated with suitable wave length to photoactivate photosensitizers. The wound bed is kept free of microbial infection thus hastening the healing process.

Example 2

Using Collagen Material and Liposomal Formulation of mTHPC to Reduce Wrinkle and Scares Overtime and with exposure to environmental factors skins begins to age and the collagen producing cell in the skin called fibroblast gradually reduces in number. The visible effect is thinning of skin and appearance of lines and wrinkles. Cut appropriate piece of the collagen sponge or take out the needed amount of collagen fibrils which is saturated with liposomal formulation of mTHPC of required concentration (1.5 ng/ml mTHPC). Such a pre-treated collagen material is placed in the area to be treated by making small cut in the skin with the help of a scalpel. After 30 minutes of incubation the area is irradiated with light energy of 10 J/cm$^2$ (100 mW/cm$^2$). The PDT treated area is then covered with surgical dressing. The collagen matrix will promote cell growth thus correcting the soft tissue contour deficiencies such as wrinkle and acne scares.

Example 3

Treating Periodontitis

In this case of periodontal disease, bacteria coating the tooth (plaque) attacked the substance that holds the tooth in place: The supporting tissue around the tooth has been broken down, the tissue which surrounds the root and the surrounding bone have been destroyed. This region is treated with liposomal formulated mTHPC and collagen matrix; after the incubation period the region is irradiated with light energy of 10 J/cm$^2$. The new collagen matrix is well accepted and yields good cosmetic results. PDT effect in this invention is also beneficial for killing sub-gingival bacteria in the region as well thus fasten the healing in the region.

Example 4

Injectable Form of Collagen as Dermal Filler

To remove the scare, wrinkles and other skin imperfection especially in face and neck region for cosmetic purpose: In such cases Foslip is injected into the treat region subcutaneously, followed by irradiation with electromagnetic radiation and final injecting Zyplast under the skin to smooth the wrinkles. Zyplast® (Inamed Aesthetics Inc.) is a form of injectable collagen that is cross linked with chemical glutaraldehyde, or the Foslip is incorporated previously mixed with Zyplast Example 5a Bone and Cartilage Repair Bone and cartilage injury can also be treated using this invention, the collagen based materils like Chondro-Gide®, Chondrocell® can be used along with liposomal formulated mTHPC and PDT to help grow the worn out or broken cartilage and bones.

Example 5b

Post PDT Photomodulation

In another embodiment of this invention Laser light of 980 nm is used post PDT period at the treated area for photomodulation. Cell activity is modified using light sources.

Example 6

Use of Adipose Tissue as Matrix

The adipose tissue first is suctioned of giber area and prepared to graft in the sulcus or soft tissue deformities after is annexed the Foslip (final tissue concentration between 1.5 to 3 ng/g of fat graft tissue) then is ready to fill the area and finally in 24 hours make tea light activation. It is an autologous fat injection. A portion of the fat tissue behaves as a graft and the rest is destroyed and incorporated like collagen matrix to the treatment area. The PDT action helps the good collagen matrix incorporation basically by maintaining the extra cellular matrix equilibrium thus improving new collagen formation This invention is not limited in its application to only examples specified in the above example, but also includes dental application, cardiovascular, wound healing and cosmetic application. One dental application is the treatment of periodontal pockets.

Having described preferred embodiments of the invention with reference to the accompanying drawings, it is to be understood that the invention is not limited to the precise embodiments, and that various changes and modifications may be effected therein by those skilled in the art without departing from the scope or spirit of the invention as defined in the appended claims.

What is claimed is:

1. A biocompatible composition suitable for use in tissue regeneration and wound healing comprising: at least one biocompatible tissue matrix with pegylated liposomes encapsulating a photosensitizer comprising temoporfin impregnated in the tissue matrix and at least one growth factor, wherein said biocompatible tissue matrix is a biodegradable matrix material selected from the group consisting of a hydrogel, a polymer, a glycoprotein, a collagen, an adipose, a non-animal stabilized hyaluronic acid, a polysaccharide, a polypeptide, and combinations thereof.

2. The composition according to claim 1, wherein said at least one growth factor is selected from the group consisting of epidermal growth factor, platelet derived growth factor, tissue angiogenesis growth factor, cytokines and combinations thereof.

3. The composition according to claim 1, wherein said photosensitizer is pegylated.

4. The composition according to claim 1, wherein the biocompatible tissue matrix comprises a dermal component.

5. A biocompatible composition suitable for use in tissue regeneration and wound healing comprising: a biocompatible tissue matrix with pegylated liposomes encapsulating a photosensitizer comprising temoporfin impregnated in the tissue matrix and a growth factor, wherein the biocompatible tissue matrix is collagen and the growth factor is selected from the group consisting of epidermal growth factor, platelet derived growth factor, tissue angiogenesis growth factor, cytokines and combinations thereof.

6. A biocompatible composition suitable for use in tissue regeneration and wound healing comprising: a biocompatible tissue matrix with pegylated liposomes encapsulating a photosensitizer comprising temoporfin impregnated in the tissue matrix and a growth factor, wherein the biocompatible tissue matrix comprises a dermal component.

7. A biocompatible composition suitable for use in tissue regeneration and wound healing comprising: at least one biocompatible tissue matrix with pegylated liposomes encapsulating a photosensitizer comprising temoporfin impregnated in the tissue matrix and at least one cellular component, wherein said biocompatible tissue matrix is a biodegradable matrix material selected from the group consisting of a hydrogel, a polymer, a glycoprotein, a collagen, an adipose, a non-animal stabilized hyaluronic acid, a polysaccharide, a polypeptide, and combinations thereof.

8. The composition according to claim 7, wherein said at least one cellular component is selected from the group consisting of keratinocytes, epidermal cells, fibroblasts and combinations thereof.

9. The composition according to claim 7, wherein said photosensitizer is pegylated.

* * * * *